(12) United States Patent
Ji et al.

(10) Patent No.: US 10,617,725 B2
(45) Date of Patent: Apr. 14, 2020

(54) **COMPOSITION CONTAINING *BIFIDOBACTERIUM* FOR ALLEVIATING, PREVENTING OR TREATING RHEUMATOID ARTHRITIS**

(71) Applicants: BIFIDO CO., LTD., Gangwon-do (KR); THE CATHOLIC UNIVERSITY OF KOREA INDUSTRY—ACADEMIC COOPERATION FOUNDATION, Seoul (KR)

(72) Inventors: Geun Eog Ji, Seoul (KR); Yunju Jeong, Seoul (KR); Hui Fang, Seoul (KR); Bin Kwon, Gangwon-do (KR); Sung-Hwan Park, Seoul (KR); Mi-La Cho, Seoul (KR); Ji-Hyeon Ju, Seoul (KR); Seung-Ki Kwok, Seoul (KR); Jennifer Lee, Seoul (KR); Ji-Won Kim, Seoul (KR); Seon-Yeong Lee, Seoul (KR); Jun-Geol Ryu, Seoul (KR); Joo-Yeon Jhun, Seoul (KR); Jae-yoon Ryu, Seoul (KR); Hyeon-Beom Seo, Seoul (KR)

(73) Assignees: BIFIDO CO., LTD., Gangwon-do (KR); THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 15/977,466

(22) Filed: May 11, 2018

(65) Prior Publication Data
US 2019/0231830 A1      Aug. 1, 2019

(30) Foreign Application Priority Data

Jan. 31, 2018 (KR) .................. 10-2018-0012354

(51) Int. Cl.
| | | |
|---|---|---|
| *B01J 31/02* | (2006.01) | |
| *A61K 35/745* | (2015.01) | |
| *A61K 9/14* | (2006.01) | |
| *A61P 19/02* | (2006.01) | |
| *A23L 33/135* | (2016.01) | |
| *A61K 9/00* | (2006.01) | |

(52) U.S. Cl.
CPC .......... *A61K 35/745* (2013.01); *A23L 33/135* (2016.08); *A61K 9/0053* (2013.01); *A61K 9/14* (2013.01); *A61P 19/02* (2018.01); *A23Y 2300/25* (2013.01)

(58) Field of Classification Search
None
See application file for complete search history.

(56) References Cited

U.S. PATENT DOCUMENTS

2014/0056852 A1* 2/2014 Guglielmetti ......... A23L 33/135
424/93.4

FOREIGN PATENT DOCUMENTS

KR       10-2011-0035100 A       4/2011

OTHER PUBLICATIONS

Feng et al., English Translation of CN104546945 publised in Chinese on Apr. 29, 2015, 57 pgs (Year: 2015).*
Riedel et al. "Interaction of bifidobacteria with Caco-2 cells—adhesion and impact on expression profiles" International Journal of Food Microbiology 110 (2006) 62-68 (Year: 2006).*
Zamani et al. "Clinical and metabolic response to probiotic supplementation in patients with rheumatoid arthritis: a randomized, double-blind, placebo-controlled trial" International Journal of Rheumatic Diseases 2016; 19: 869-879 (Year: 2016).*
Coore et al. "Production of Concentrated Bifidobacterium bifidum" J. Chem. Tech. Biotechnol 1992, 53, pg. 189-194 (Year: 1992).*
Dinakar et al. "Growth and Viability of *Bifidobacterium bifidum* in Cheddar Cheese" J Dairy Sci 77:2854-2864, 1994 (Year: 1994).*
Vinderola et al. "Culture media for the enumeration of *Bifidobacterium bifidum* and *Lactobacillus acidophilus* in the presence of yoghurt bacteria" International Dairy Journal 9 (1999) 497}505 (Year: 1999).*

* cited by examiner

*Primary Examiner* — Thane Underdahl
(74) *Attorney, Agent, or Firm* — Vorys, Sater, Seymour and Pease LLP; Mih Suhn Koh

(57) ABSTRACT

Provided is a composition containing *Bifidobacterium* for alleviating, preventing or treating rheumatoid arthritis. The *Bifidobacterium bifidum* ATT newly isolated according to the present invention is useful as a rheumatoid arthritis medicine or a probiotic material for alleviating rheumatoid arthritis owing to potent efficacy in treating rheumatoid arthritis.

3 Claims, 6 Drawing Sheets

COMPOSITION CONTAINING *BIFIDOBACTERIUM* FOR ALLEVIATING, PREVENTING OR TREATING RHEUMATOID ARTHRITIS

BACKGROUND OF THE INVENTION

Field of the Invention

The present invention relates to a composition containing *Bifidobacterium* for alleviating, preventing or treating rheumatoid arthritis.

Description of the Related Art

Degenerative arthritis is the most common inflammatory disease of the joints, which involves inflammation and pain, when bones and ligaments constituting the joints are damaged due to progressive damage or degenerative changes in the cartilage that protects the joints. Degenerative arthritis is classified into primary (idiopathic) arthritis which occurs by factors such as age, gender, genetic factors, obesity, specific joint sites and the like, without specific congenital factors, and secondary (subsequent) arthritis caused by trauma, disease, deformity and the like that may damage the articular cartilage.

Meanwhile, rheumatoid arthritis is a chronic inflammatory disease characterized by inflammation and proliferation of synovial cells. Rheumatoid arthritis induces osteoporosis, bone erosion and so on, unlike degenerative arthritis. Rheumatoid arthritis progresses in the following stages: inflammation of the synovial membrane spreads into the joint capsule, ligament and tendon (stage 1); the gap between the joints becomes narrow and the tension between the joint membrane and ligament disappears due to gradual destruction of the joint cartilage (stage 2); inflammation penetrates into the bones, causing partial erosion of the bones (stage 3); and the joint function is lost (stage 4).

For the treatment of rheumatoid arthritis, non-steroidal anti-inflammatory drugs (NSAIDs/NAIDs) such as NSAIDs, salicylates and COX-2 inhibitors; adrenal cortical hormone drugs such as prednisolone and triamcinolone; disease-modifying antirheumatic drugs (DMARDs) such as methotrexate and sulfasalazine; and biologics such as etanercept, infliximab and adalimumab have been conventionally used.

Typically, non-steroidal anti-inflammatory drugs and adrenocortical hormone preparations are used in the early stage of symptom onset, and antirheumatic drugs are used in consideration of symptoms and disease activity. In severe cases, biologics or combination therapies are used in clinical practice.

However, biologics have a problem of inapplicability to the medical field because of costly treatment costs compared to conventional therapeutic agents. Disadvantageously, non-steroidal anti-inflammatory drugs such as NSAIDs, which entail relatively low treatment costs, cause gastrointestinal side effects, and antirheumatic drugs such as methotrexate and sulfasalazine also cause gastrointestinal disorders.

Therefore, there is an urgent need to develop novel medicines that have therapeutic effects of rheumatoid arthritis, while overcoming the limitations of conventional treatment methods.

PATENT DOCUMENT (Patent Document 1) Korean Patent Laid-open No. 10-2011-0035100 (Apr. 6, 2011) discloses a method for producing a herbal composition for treating osteoarthritis containing a Kalopanax bark extract biotransformed by *Saccharomyces cerevisiae* mutant BH02 or *Saccharomyces exiguus* mutant BH12.

SUMMARY OF THE INVENTION

Therefore, the present invention has been made in view of the above problems, and it is an object of the present invention to isolate a novel microorganism effective for alleviating, preventing or treating rheumatoid arthritis and provide a method of using the microorganism.

In accordance with the present invention, the above and other objects can be accomplished by the provision of a *Bifidobacterium bifidum* ATT (accession number: KCTC13474BP) effective for preventing or treating rheumatoid arthritis.

In accordance with another aspect of the present invention, there is provided a food composition for alleviating rheumatoid arthritis comprising a culture solution of *Bifidobacterium bifidum* ATT (accession number: KCTC13474BP), or a dried powder thereof.

In accordance with another aspect of the present invention, there is provided a pharmaceutical composition for preventing or treating rheumatoid arthritis comprising a culture solution of *Bifidobacterium bifidum* ATT (accession number: KCTC13474BP), or a dried powder thereof.

BRIEF DESCRIPTION OF THE DRAWINGS

The above and other objects, features and other advantages of the present invention will be more clearly understood from the following detailed description taken in conjunction with the accompanying drawings, in which.

Figure 1:
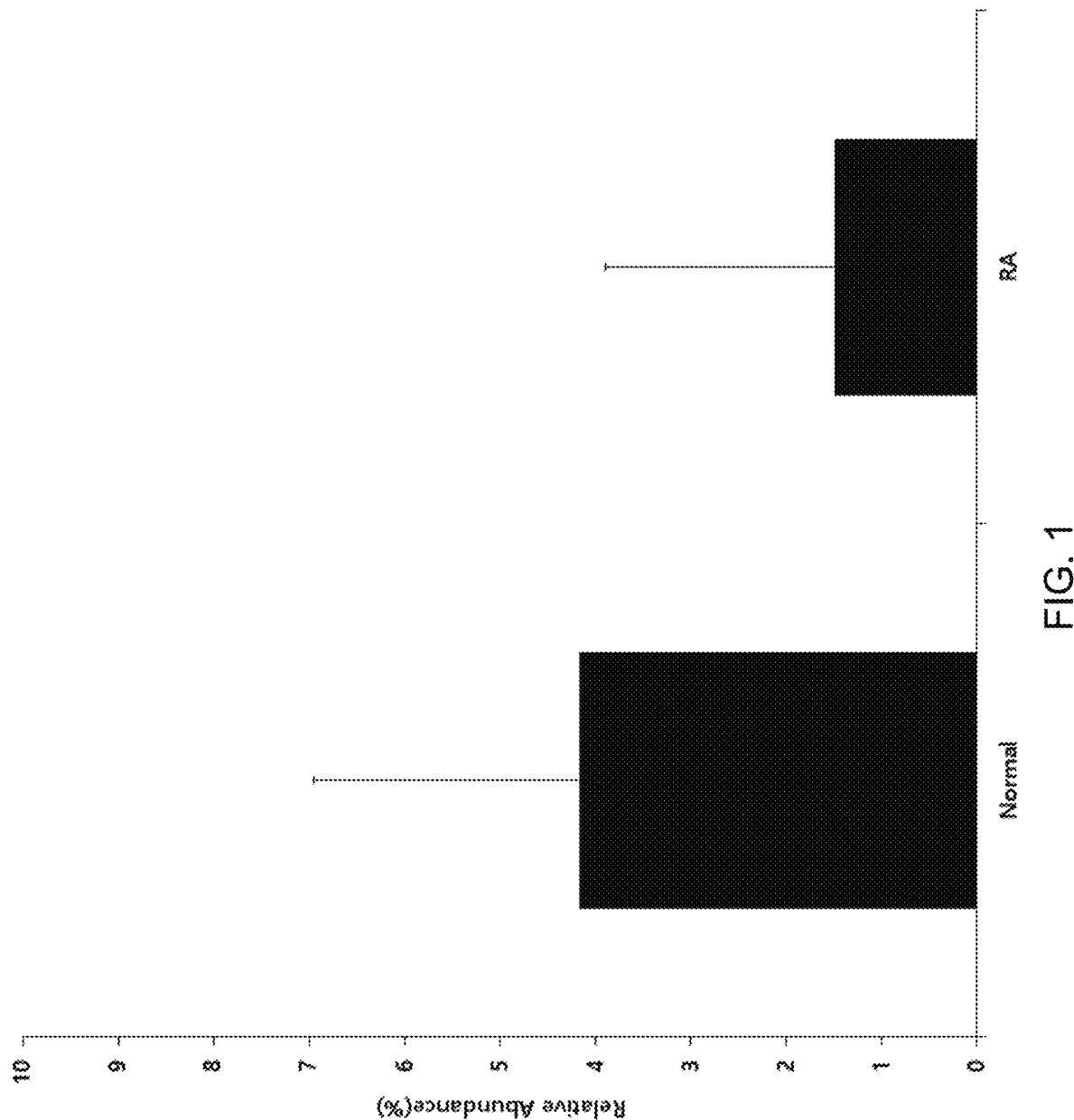
FIG. 1 shows an analysis result of intestinal microbial flora distributions on normal subjects and Korean rheumatoid arthritis patients (Normal: normal subject, RA: rheumatoid arthritis patient)

*bacterium biffidum* ATT: group to which *Bifidobacterium bifidum* ATT is administered; p<0.05*).

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

The present invention provides *Bifidobacterium bifidum* ATT (accession number: KCTC13474BP) effective for preventing or treating rheumatoid arthritis. The present invention proved that *Bifidobacterium bifidum* ATT is capable of being highly adhered to intestinal cells, slowing down the onset of rheumatoid arthritis and significantly reducing the incidence of rheumatoid arthritis.

Accordingly, the present invention provides a food composition for alleviating rheumatoid arthritis which contains a culture solution of *Bifidobacterium bifidum* ATT (accession number: KCTC13474BP) or a dried powder thereof. Regarding the food composition for alleviating rheumatoid arthritis according to the present invention, the *Bifidobacterium bifidum* ATT is preferably present in an amount of 0.00001 to 50% by weight with respect to the weight of the food composition for alleviating rheumatoid arthritis. When the *Bifidobacterium bifidum* ATT is present in an amount of less than 0.00001% by weight, effects thereof are unsatisfactory, and when the *Bifidobacterium bifidum* ATT is present in an amount higher than 50% by weight, the effects thereof are poor, compared to the amount of *Bifidobacterium bifidum* ATT used, thus making it less economical.

For example, the food composition for alleviating rheumatoid arthritis according to the present invention is selected from the group consisting of meat, cereal, caffeinated beverages, regular beverages, chocolate, bread, snacks, confectionery, candy, pizza, jelly, noodles, gums, dairy products, ice cream, alcoholic beverages, alcoholic drinks, vitamin complexes and other health supplement foods, but the present invention is not limited thereto.

The present invention provides a pharmaceutical composition for preventing or treating rheumatoid arthritis which contains a culture solution of *Bifidobacterium bifidum* ATT (accession number: KCTC13474BP) or a dried powder thereof.

Meanwhile, the pharmaceutical composition for preventing or treating rheumatoid arthritis according to the present invention may further include a pharmaceutically acceptable carrier, diluent or excipient, in addition to the active ingredient. Examples of suitable carriers, excipients or diluents include lactose, dextrose, sucrose, sorbitol, mannitol, xylitol, erythritol, maltitol, starch, acacia gum, alginate, gelatin, calcium phosphate, calcium silicate, cellulose, methylcellulose, amorphous cellulose, polyvinylpyrrolidone, water, methylhydroxybenzoate, propylhydroxybenzoate, talc, magnesium stearate, mineral oil and a combination thereof. In addition, the drug, which is the pharmaceutical composition for preventing or treating rheumatoid arthritis according to the present invention, may further include one or more selected from fillers, anti-coagulants, lubricants, wetting agents, perfumes, emulsifiers and preservatives.

Meanwhile, the pharmaceutical composition for preventing or treating rheumatoid arthritis according to the present invention is preferably formulated depending on application method. In particular, the pharmaceutical composition is preferably formulated by selecting a method well-known in the art to provide rapid, sustained or delayed release of the active ingredient after administration to mammals. Specifically, examples of the formulation may include any one selected from plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, cataplasma, capsules, creams, troches, tinctures, pastes, pills, and soft or hard gelatin capsules.

Meanwhile, the dose of the pharmaceutical composition for preventing or treating rheumatoid arthritis according to the present invention is preferably determined in consideration of method of administration, age, gender and weight of patients and severity of diseases. For example, the pharmaceutical composition for preventing or treating rheumatoid arthritis according to the present invention can be administered at least once in a daily dose of 0.00001 to 100 mg/kg (body weight). However, the dose is provided as an example and can be changed by the physician's prescription depending on the conditions of a patient.

Hereinafter, the present invention will be described in more detail with reference to the following Example or Test Example. The scope of the present invention is not limited to the following Example or Test Example, and includes modifications of the technical concept equivalent thereto.

Example 1: Confirmation of Effects of *Bifidobacterium bifidum* ATT on Rheumatoid Arthritis (1) Confirmation of Intestinal Microbial Flora Distributions of Korean Rheumatoid Arthritis Patients In order to analyze the intestinal microbial flora composition of rheumatoid arthritis patients, fecal samples were collected from 3 normal subjects and 79 Korean rheumatoid arthritis patients, and stored at −80° C. Then, in order to conduct next generation sequencing on the fecal samples, bacterial genomic DNAs were isolated from the fecal samples and 16S rRNA genes specific to microorganisms were amplified to produce a library. The 16S rRNA genes of the library were decoded using Misep available from Illumina Inc. The decoded sequences were subjected to bioinformatic analysis using QIIME1.9.1 (open-source bioinformatic pipeline) (FIG. 1). FIG. 1 shows an analysis result of intestinal microbial flora distributions on normal subjects and Korean rheumatoid arthritis patients (Normal: normal subject, RA: rheumatoid arthritis patient). The analysis result of intestinal microbial flora showed that the rheumatoid arthritis patient group exhibited a decrease in *Bifidobacterium* genus compared to the normal subjects (p=0.03).

(2) Confirmation of Intestinal Microbial Flora Distribution Depending on Stages and Treatment Methods of Korean Rheumatoid Arthritis Patients In order to analyze the intestinal microbial flora composition in rheumatoid arthritis patients, 3 normal subjects (Normal group) and 79 Korean rheumatoid arthritis patients were classified, based on stages and treatment methods, into five groups in total, that is, a group with no rheumatoid arthritis symptom (Preclinical rheumatoid arthritis), a group diagnosed with rheumatoid arthritis (Drug Naive Rheumatoid Arthritis), a group treated with an antirheumatic drug (Conventional DMARD; methotrexate (MTX)), a group treated with a primary biologic (Biologic, BL; TNF inhibitor) and a group treated with a secondary biologic (2nd Biologic, BS; IL-6R mAb, CTLA4-Ig). The group with no rheumatoid arthritis symptom (Preclinical Rheumatoid Arthritis) means a group of patients who show an increase in RA (rheumatoid arthritis) index, but have no rheumatoid arthritis symptoms, and the group diagnosed with rheumatoid arthritis (Drug Naive Rheumatoid Arthritis) means a group of patients who are diagnosed with rheumatoid arthritis, but do not take any drug.

Figure 2:
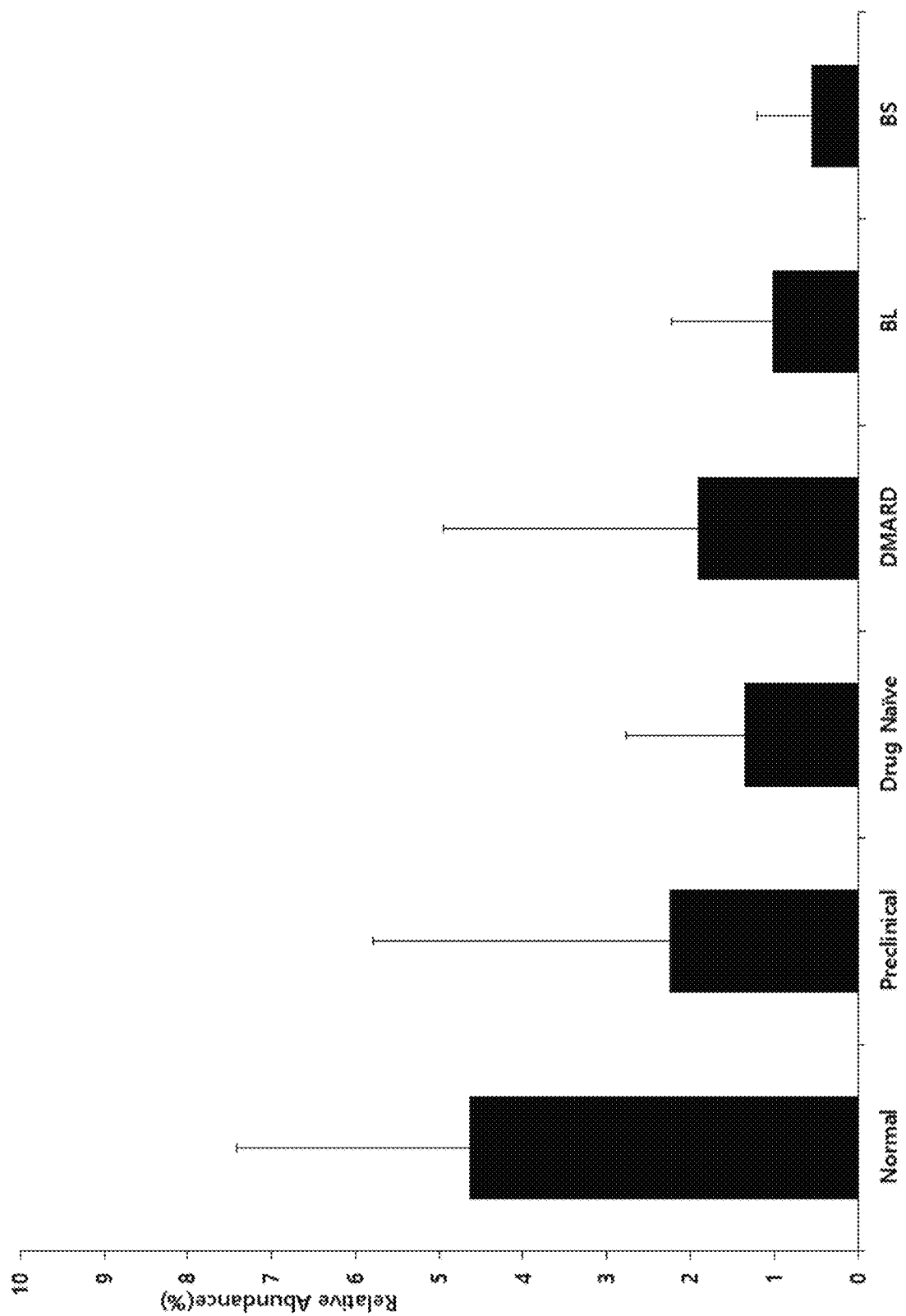
FIG. 2 shows an analysis result of intestinal microbial flora distributions depending on stage and treatment method on normal subjects and Korean rheumatoid arthritis patients (Normal: normal group, Preclinical: group with no rheumatoid arthritis symptom, Drug Naive: group diagnosed with rheumatoid arthritis, DMARD: group treated with an anti-rheumatic drug (methotrexate (MTX)), BL: group treated with a primary biologic (TNF inhibitor), BS: group treated with a secondary biologic (IL-6R mAb, CTLA4-Ig))

Then, fecal samples were collected from the subjects' fecal samples and stored at −80° C. Then, in order to conduct next generation sequencing on the fecal samples, bacterial genomic DNAs were isolated from the fecal samples and 16S rRNA genes specific to microorganisms were amplified to produce a library. The 16S rRNA genes of the library were decoded using Misep available from Illumina Inc. The decoded sequences were subjected to bio-informatic analysis using QIIME1.9.1 (open-source bioinformatic pipeline) (FIG. 2). FIG. 2 shows an analysis result of intestinal microbial flora distribution depending on stage and treatment method on normal subjects and Korean rheumatoid arthritis patients (Normal: a normal group, Preclinical: a group with no rheumatoid arthritis symptom, Drug Naive: a group diagnosed with rheumatoid arthritis, DMARD: a group treated with an antirheumatic drug (methotrexate (MTX)), BL: a group treated with a primary biologic (TNF inhibitor), BS: a group treated with a secondary biologic (IL-6R mAb, CTLA4-Ig)).

As a result of analysis of the intestinal microbial flora distributions in the normal group and five drug administration groups, it can be seen that, as reaction to the rheumatoid arthritis drug decreases, compared to the normal group, *Bifidobacterium* spp. is decreased. The patient group, to which a biologic is firstly administered, does not react to DMARD, which is a conventional drug and thus shows lower *Bifidobacterium* distribution than the DMARD group and much lower *Bifidobacterium* distribution than the normal subject (p-value<0.01). The patient group, to which a biologic is secondarily (or tertiary) administered, does not react to the primary biologic and thus shows the lowest *Bifidobacterium* distribution among all the groups, and shows a significant decrease in *Bifidobacterium* distribution as compared to the normal subject (p<0.01).

(3) Isolation of *Bifidobacterium* Spp.

The present inventors chose a variety of *Bifidobacterium* genera from human feces, chose *Bifidobacterium bifidum* ATT effective for treating rheumatoid arthritis through preliminary tests, deposited at the Korea Research Institute of Bioscience and Biotechnology on Jan. 30, 2018, and then received an accession number of KCTC13474BP.

Figure 3:
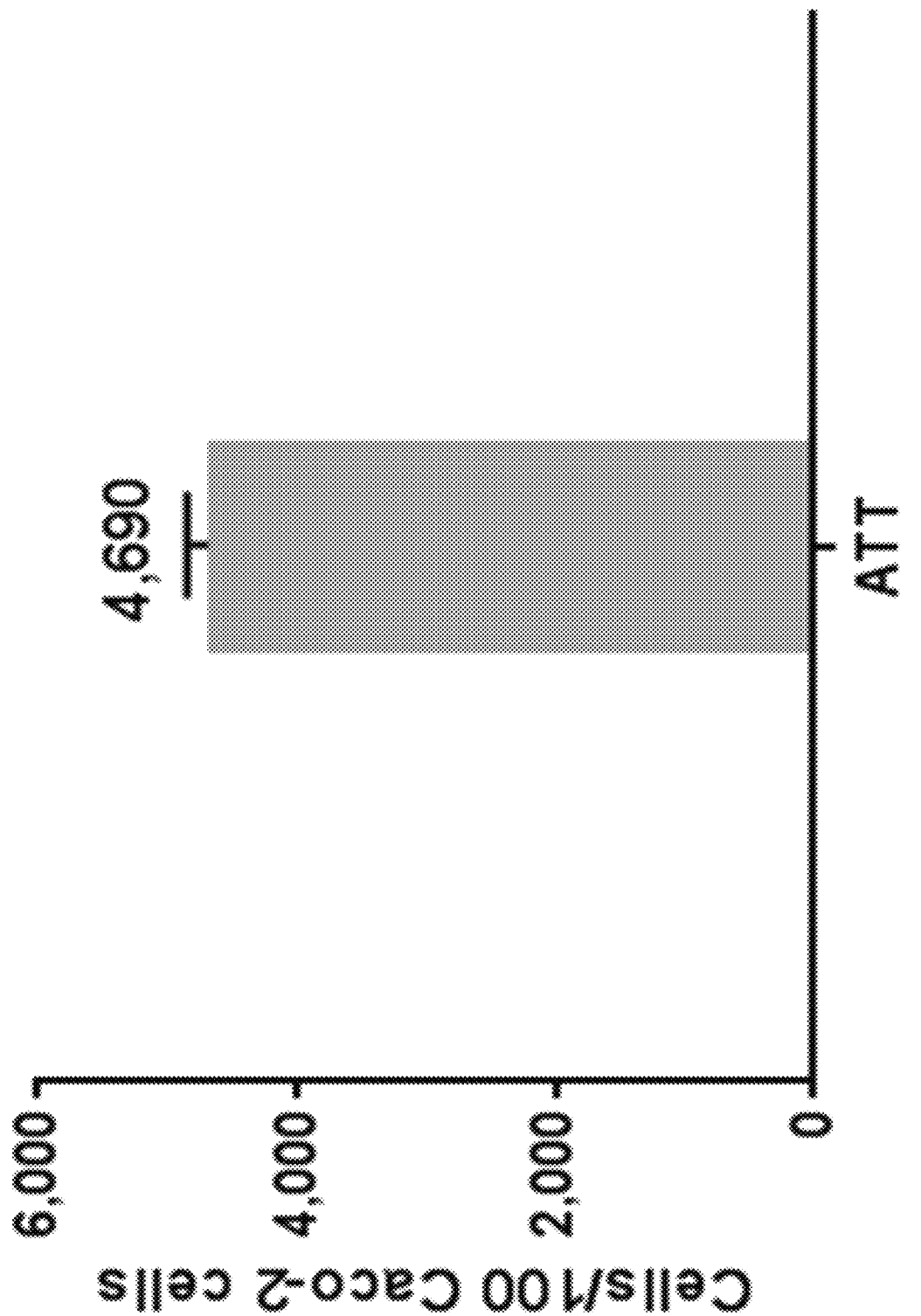
FIG. 3 shows an analysis result of adhesion to the intestine of the *Bifidobacterium bifidum* ATT found by the present invention.

Test Example 1: Confirmation of Adhesion to Intestine of *Bifidobacterium bifidum* ATT In order to ascertain the ability of *Bifidobacterium bifidum* ATT to be adhered to the intestine found by the present invention, the human colonic epithelial cell line, Caco-2 was seeded at a concentration of $1\times10^5$ cells/well on a 24-well plate and cultured for 14 days. Then, the cells were treated with $1\times10^8$ CFU of *Bifidobacterium bifidum* ATT having been cultured in MRS liquid medium for 18 hours and then cultured for 1 hour. After culturing for one hour, a beneficial bacteria suspension was injected into the cells, the cells were washed with PBS three times to remove the remaining cells and were harvested with trypsin EDTA, and the genomic DNAs were extracted. A standard curve was drawn using qPCR with a primer specific to the *Bifidobacterium bifidum* ATT, and the amount of *Bifidobacterium bifidum* ATT contained in the genomic DNAs extracted in the sample was weighed to check adhesion capability (FIG. 3). FIG. 3 shows an analysis result of adhesion to the intestine of the *Bifidobacterium bifidum* ATT found by the present invention. According to Candela's method (Candela M, Seibold G, Vitali B, Lachenmaier S, Eikmanns B J and Brigidi P. 2005. Research in Microbiology. 156: 887-895.), the adhesion of bacteria is strong when the number of bacteria adhered to 100 Caco-2 cells is more than 40. In consideration of this standard, the *Bifidobacterium bifidum* ATT exhibits considerably excellent adhesion to intestinal cells.

Figure 4:
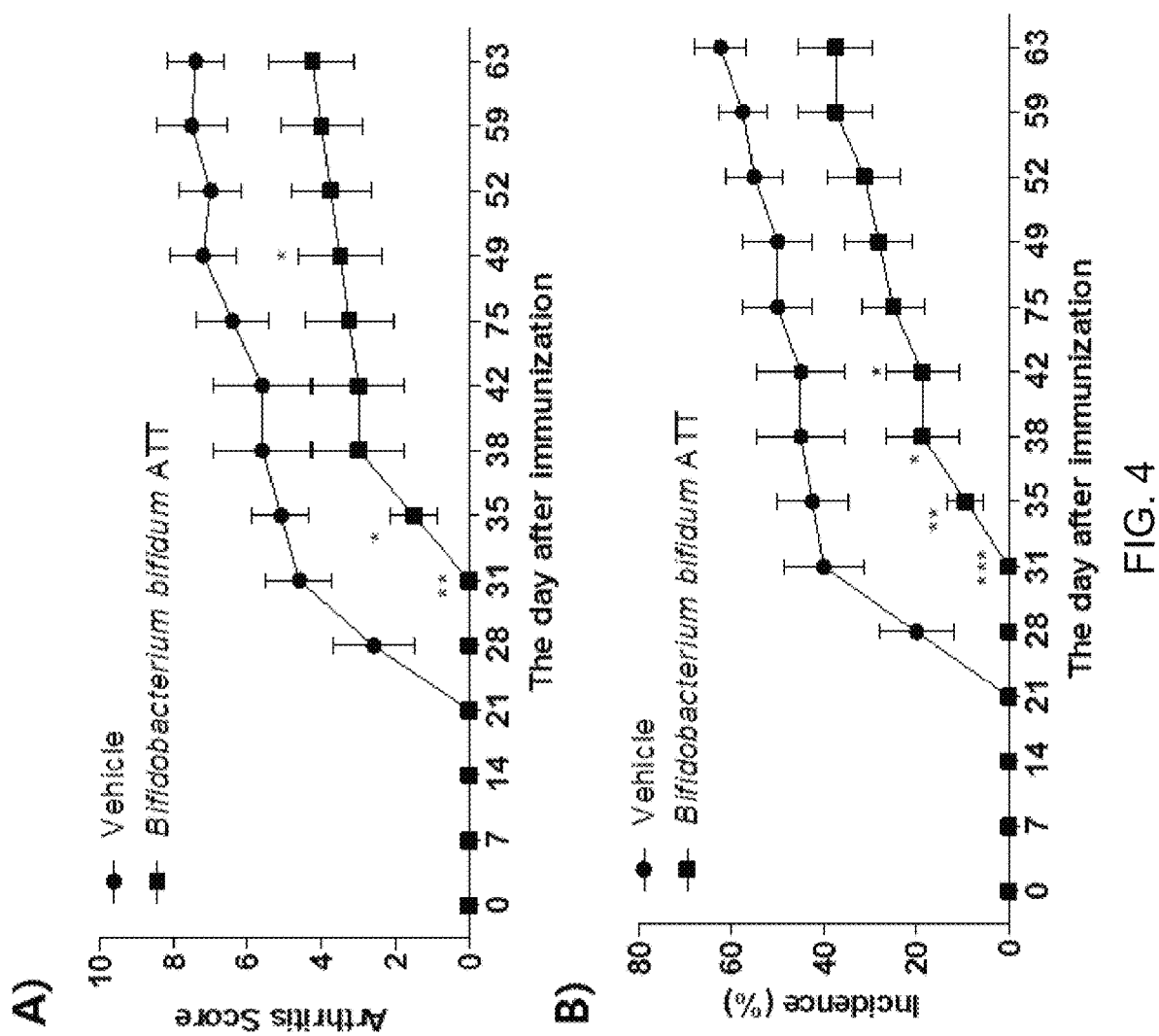
FIG. 4 shows an analysis result of a control effect of *Bifidobacterium bifidum* ATT on rheumatoid arthritis [(A) comparison in rheumatoid arthritis score ($p<0.001*$, $p<0.01$, $p<0.05*$), (B) comparison in rheumatoid arthritis incidence ($p<0.001*$, $p<0.01$, $p<0.05*$)]

Test Example 2: Confirmation of Inhibitory Effect of *Bifidobacterium bifidum* ATT on Secretion of IL-8 in Human Colon Cancer Cell Line In order to confirm whether *Bifidobacterium bifidum* ATT inhibits secretion of IL-8 in the human colon cancer cell line, *Bifidobacterium bifidum* ATT was orally administered at a concentration of 100 mg/kg to rheumatoid arthritis subjects daily for one week after the onset of rheumatoid arthritis. Rheumatoid arthritis started to develop 21 days after disease induction, and the group, to which *Bifidobacterium bifidum* ATT was administered, started to develop the disease 30 days after disease induction, but showed significant inhibition of the disease, compared to the rheumatoid arthritis control group. The incidence of rheumatoid arthritis was significantly inhibited in the group to which *Bifidobacterium bifidum* ATT was administered (FIG. 4). FIG. 4 shows an analysis result of a control effect of *Bifidobacterium bifidum* ATT on rheumatoid arthritis [(A) comparison in rheumatoid arthritis score ($p<0.001$*, $p<0.01$, $p<0.05$*), (B) comparison in rheumatoid arthritis incidence ($p<0.001$*, $p<0.01$, $p<0.05$*)].

Figure 5:
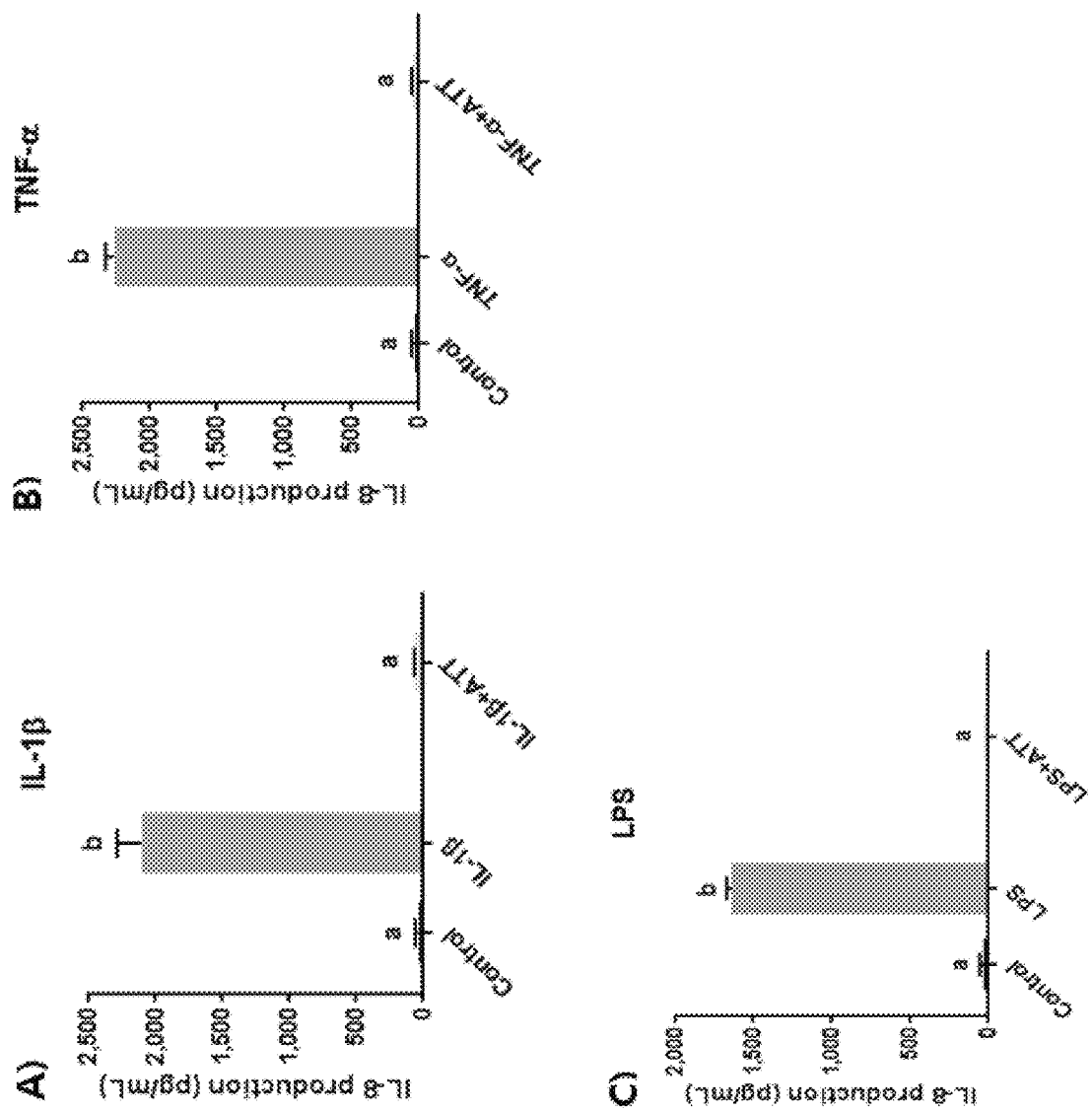
FIG. 5 shows an analysis result of inhibition on IL-8 secretion of *Bifidobacterium bifidum* ATT in human colon cancer cell line HT-29 [(A) IL-1β treatment group, (B) TNFα treatment group, (C) LPS treatment group]

Test Example 3: Confirmation of Inhibitory Effect of *Bifidobacterium bifidum* ATT on Development of Rheumatoid Arthritis In order to weigh the amount of inflammatory factor IL-8 (interleukin 8) secreted in the human colon cancer cell (HT-29 cell) line, IL-1β, TNF-α and LPS as stimulus sources, and *Bifidobacterium bifidum* ATT ($1\times10^8$ CFU/ml) were applied to the HT-29 cell monolayer and cultured for 6 hours. To assay IL-8 secreted from the cells, the supernatant was collected and analyzed using a Human IL-8 ELISA Set (BD, San Diego, USA) (FIG. 5). FIG. 5 shows an analysis result of inhibition on IL-8 secretion of *Bifidobacterium bifidum* ATT in human colon cancer cell line HT-29 [(A) IL-1β treatment group, (B) TNFα treatment group, (C) LPS treatment group]. When *Bifidobacterium bifidum* ATT was treated in combination with three stimulus sources (IL-1β, TNF-α, LPS), IL-8 expression caused by the stimulus sources was similar to that of the non-treatment group and was significantly decreased, compared to the group treated with one kind of stimulus source ($p<0.05$).

Figure 6:
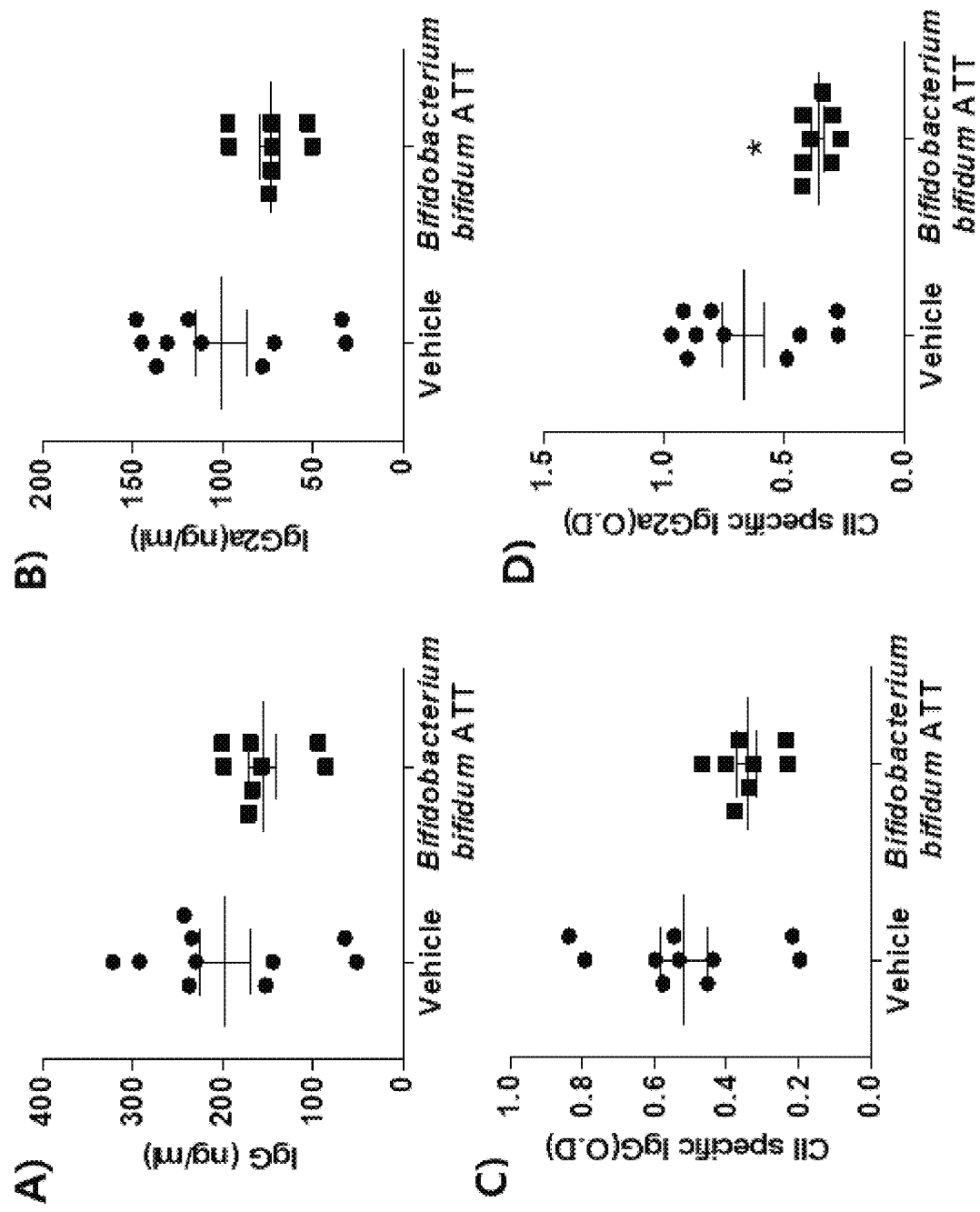
FIG. 6 shows an analysis result of IgG antibody expression in the rheumatoid arthritis-induced mouse serum [(A): IgG, (B): IgG2a, (C): IgG specific to rheumatoid arthritis antibody (type ii collagen; Cii) (Cii-specific IgG), (D): IgG2a specific to rheumatoid arthritis antibody (type ii collagen; Cii) (Cii-specific IgG2a); Vehicle: group to which *Bifidobacterium bifidum* ATT is not administered, *Bifido*-

Test Example 4: Analysis of IgG Antibody Expression in Rheumatoid Arthritis Animal Serum In order to analyze expression of IgG antibody in the mouse serum, mouse subjects of *Bifidobacterium bifidum* ATT non-treatment (Vehicle) and treatment groups (*Bifidobacterium bifidum* ATT) 63 days after induction of rheumatoid arthritis were subjected to orbital blood collection and the serum was isolated from the blood. IgG, IgG2a, IgG specific to the rheumatoid arthritis antibody (type ii collagen; Cii) (Cii-specific IgG), and IgG2a specific to the rheumatoid arthritis antibody (Cii-specific IgG2a) were measured from the isolated serum (FIG. 6). FIG. 6 shows an analysis result of IgG antibody expression in the rheumatoid arthritis-induced mouse serum [(A): IgG, (B): IgG2a, (C): IgG specific to the rheumatoid arthritis antibody (type ii collagen; Cii) (Cii-specific IgG), (D): IgG2a specific to the rheumatoid arthritis antibody (type ii collagen; Cii) (Cii-specific IgG2a); Vehicle: group to which *Bifidobacterium bifidum* ATT is not administered, *Bifidobacterium bifidum* ATT: group to which *Bifidobacterium bifidum* ATT is administered; $p<0.05*$]. The group, to which *Bifidobacterium bifidum* ATT was administered, exhibited inhibition on arthritis activity and antibody activity through a rheumatoid arthritis antigen-specific probiotic composite ($p<0.05*$).

As is apparent from the above description, the *Bifidobacterium bifidum* ATT newly isolated according to the present invention is useful as a rheumatoid arthritis medicine or a probiotic material for alleviating rheumatoid arthritis owing to potent efficacy in treating rheumatoid arthritis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

ACCESSION NUMBER

Deposition organization: Korea Research Institute of Bioscience and Biotechnology
Accession number: KCTC13474BP
Deposition date: 20180130

What is claimed is:

1. A method of treating or alleviating rheumatoid arthritis comprising administering a composition comprising an effective amount of culture solution or dried powder of *Bifidobacterium bifidum* ATT (accession number: KCTC13474BP) to a subject in need thereof.

2. The method of claim 1, wherein the composition is a food composition for alleviating rheumatoid arthritis.

3. The method of claim 1, wherein the composition is a pharmaceutical composition for treating rheumatoid arthritis.

* * * * *